(12) United States Patent
Haeussinger

(10) Patent No.: US 10,743,888 B2
(45) Date of Patent: Aug. 18, 2020

(54) POINT SPECIFIC JUNCTIONAL TOURNIQUET

(71) Applicant: John D. Haeussinger, Santee, CA (US)

(72) Inventor: John D. Haeussinger, Santee, CA (US)

( * ) Notice: Subject to any disclaimer, the term of this patent is extended or adjusted under 35 U.S.C. 154(b) by 256 days.

(21) Appl. No.: 15/904,725

(22) Filed: Feb. 26, 2018

(65) Prior Publication Data
US 2018/0193032 A1    Jul. 12, 2018

Related U.S. Application Data

(63) Continuation-in-part of application No. 15/403,149, filed on Jan. 10, 2017, now Pat. No. 9,901,368.

(51) Int. Cl.
*A61B 17/132* (2006.01)
*A61B 90/00* (2016.01)

(52) U.S. Cl.
CPC ...... *A61B 17/1325* (2013.01); *A61B 17/1327* (2013.01); *A61B 2090/0807* (2016.02)

(58) Field of Classification Search
CPC ............ A61B 17/1327; A61B 17/1325; A61B 17/1322; A61B 17/3215; A61B 2017/0042; A61B 217/00526; A61B 2017/00548; A61B 2017/00557; A61B 2090/0807; A61B 50/312; A61B 5/150305; A61F 5/012; A61F 5/0193; A61F 5/055
See application file for complete search history.

(56) References Cited

U.S. PATENT DOCUMENTS

| | | | | |
|---|---|---|---|---|
| 1,771,689 | A * | 7/1930 | Owen | A61B 17/1327 606/203 |
| 2005/0046630 | A1* | 3/2005 | Jacob | G06T 13/00 345/475 |
| 2008/0281351 | A1* | 11/2008 | Croushorn | A61B 17/1325 606/202 |
| 2013/0267994 | A1* | 10/2013 | Crowder | A61B 17/1325 606/203 |
| 2016/0058130 | A1* | 3/2016 | Boney | G01B 3/1084 24/712.6 |

* cited by examiner

*Primary Examiner* — Shaun L David
*Assistant Examiner* — Mohamed G Gabr
(74) *Attorney, Agent, or Firm* — Richard D. Clarke

(57) ABSTRACT

A point specific junctional tourniquet is provided having a rotational variable height adjustable point specific compression device including an upper housing, a lower housing rotationally nested within the upper housing and a base with an integral belt/strap guide and a belt/strap having a medical clasp, wherein for height adjustment of said upper housing and pressure form, the user grips the upper housing and the lo Aver housing and rotationally twists the two gripped housings causing the height to increase and after the optimum height is reached, depending upon the injury or wound, the assembled rotational variable height adjustable point specific compression device is secured in place and pressure is applied using the belt/strap, held in place within the belt/strap guide. The point specific junctional tourniquet is provided with a smartphone application for use in emergency situation events as required.

19 Claims, 12 Drawing Sheets

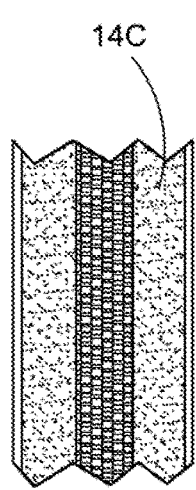 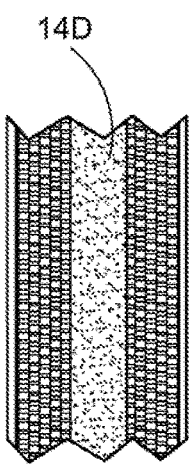 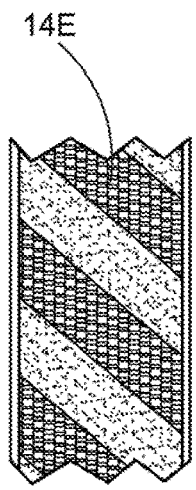 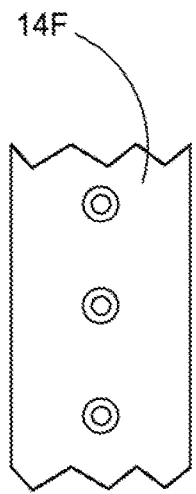
FIG. 8　　　FIG. 9　　　FIG. 10　　　FIG. 11
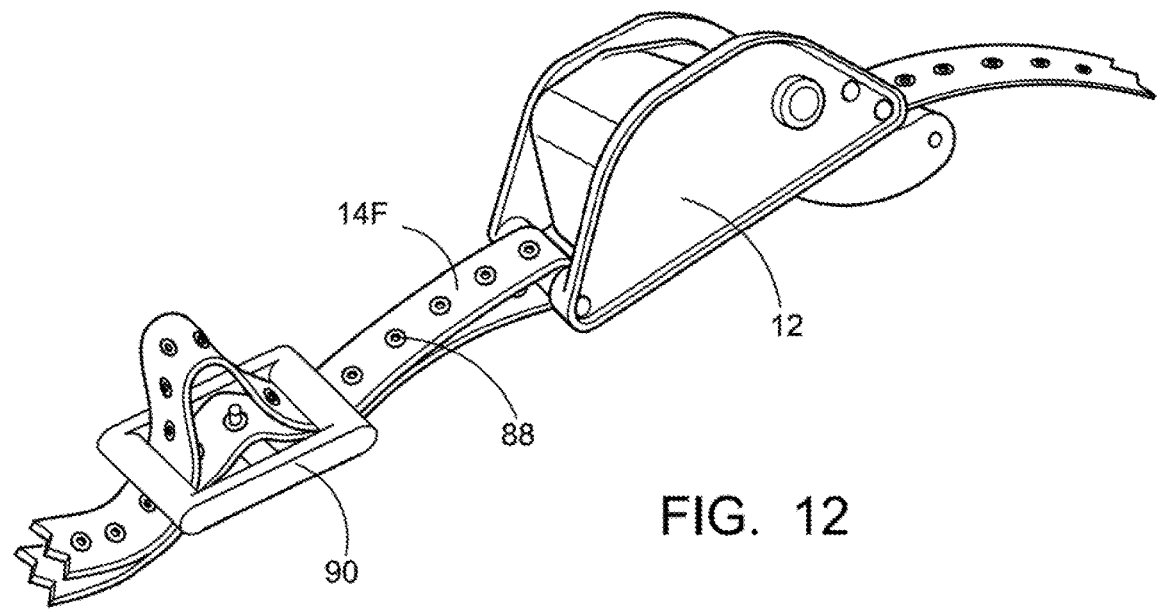
FIG. 12

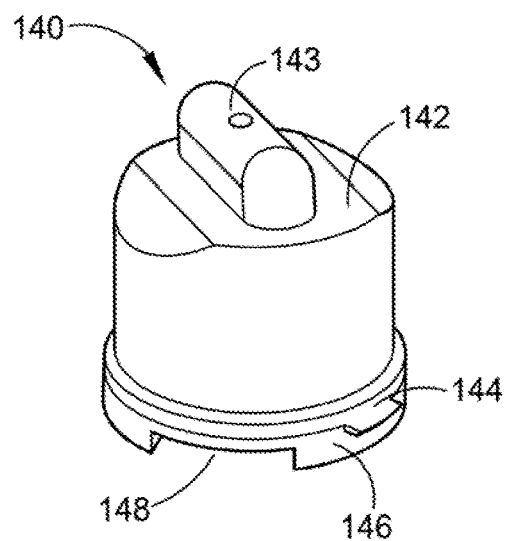
FIG. 21
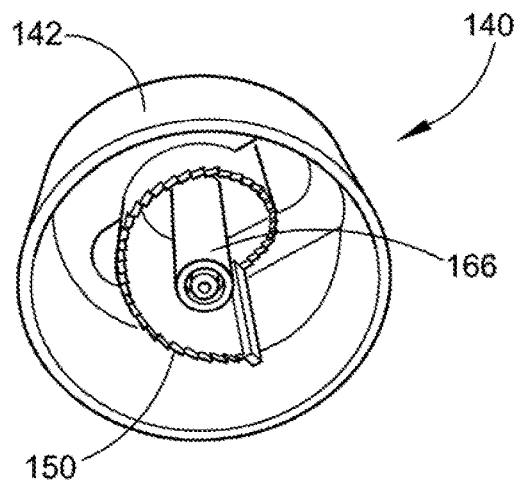
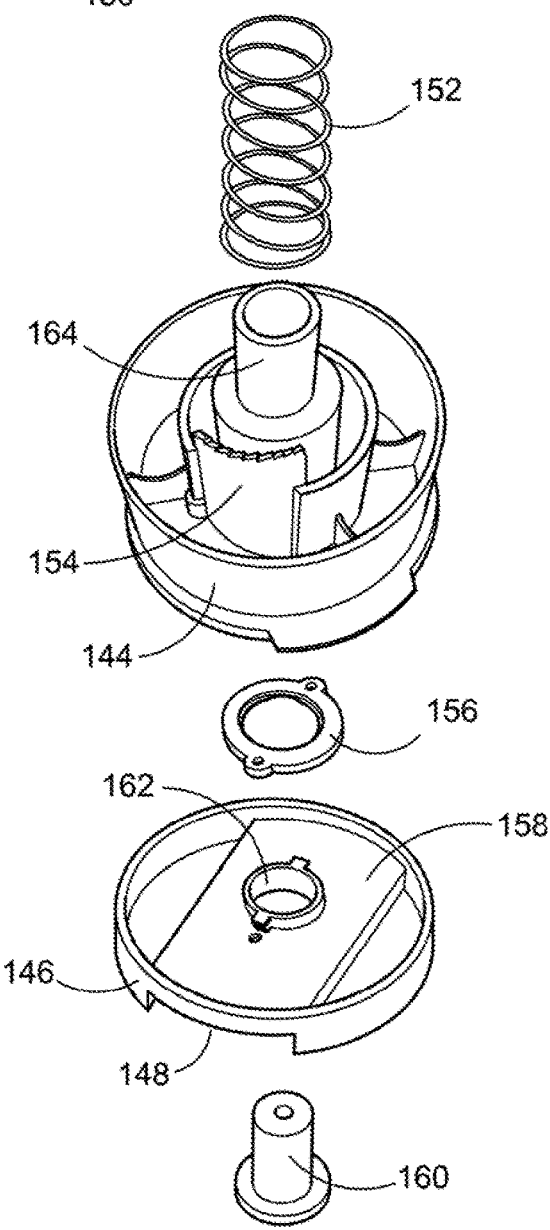
FIG. 22

POINT SPECIFIC JUNCTIONAL TOURNIQUET

FIELD OF THE INVENTION

This invention relates to a point specific junctional tourniquet for dealing with wounds involving uncontrolled hemorrhaging from the iliac, axillary and other major arteries of the body. More particularly, a variable height adjustable point specific tourniquet compression device is provided, along with a belt having a medical clasp, and a smartphone application (app) to instruct and guide the user in using the tourniquet in an emergency situation event.

BACKGROUND OF THE INVENTION

Various tourniquet devices that use a wide variety of clamping and/or pneumatic means to apply pressure to various limbs on the body have been attempted. However, prior attempts at occluding hemorrhaging from these major blood vessels of the body have not been completely successful, especially if attempted on gross battle-field wounds such as leg amputations due to anti-personnel mines or high velocity bullet percussion wounds to the lower extremities and other injuries associated with improvised explosive device (IED) detonations and the like.

This is an article where the USAMRMC is seeking information regarding novel junctional tourniquets, Junctional Tourniquets for the Department of Defense Research, on Combat Casualty Care The Combat Casualty Care Research Program of the Medical Research and Materiel Command (USAMRMC) provides integrated capabilities for far-forward medical care to reduce the mortality and morbidity associated with major battlefield wounds and injuries. The primary focus is to make possible the highest degree of medical care available in the pre-ambulance and pre-evacuation environment prior to reaching a higher level of care. The USAMRMC is seeking information regarding novel junctional tourniquets, both FDA approved and prototype devices, for hemorrhage control of junctional injuries and quadrant injuries on the battlefield including iliac and axillary.

Interested firms should submit a 1 to 3-page white paper (with additional sheets for diagrams as necessary) describing such devices and the concept of use. Information will be reviewed pursuant to consideration for the development of a request for devices to be tested. As such, any descriptions of clinical use or test and evaluation studies will be of use. For the purposes of this request for information, we anticipate that devices:

Will be able to occlude arterial bleeding from femoral, iliac, subclavian, axillary, and brachial arteries at compressible sites where standard tourniquets cannot be applied;
1. Can be point specifically (by injury type) applied and height/size adjusted easily in a tactical environment;
2. Must not slip during tightening or following application on a victim;
3. Be capable of easy release and reapplication;
4. Be of light weight, simple, and durable design;
5. Have long shelf life, low manufacturing/selling cost and of low volume when cubed into a kit pack.

While developing a Junctional Tourniquet Kit and protocol, for rural and urban law enforcement personnel, it was discovered that no practical torso tourniquets were available. To rectify the situation the Junctional Tourniquet Kit was devised, and created, that addresses, and satisfies, all of USAMRMC's "junctional tourniquet" requirements plus being a great advancement in first aide care for military as well as the civilian medical caregivers.

Numerous innovations for tourniquets have been provided in the prior art that art described as follows. Even though these innovations may be suitable for the specific individual purposes to which they address, they differ from the present Point Specific Junctional Tourniquet as hereinafter contrasted. The following is a summary of those prior art patents most relevant to the design at hand, as well as a description outlining the difference between the features of the present Point Specific Junctional Tourniquet and those of the prior art.

U.S. Pat. No 6,884,254 of Shan L. Brooks describes a tourniquet system having a strap, a clamp for selectively engaging the strap in which once the clamp engages the strap, the clamp permits the strap to pass substantially freely in a direction away from the clamp and substantially prevents the strap from passing in a direction towards the clamp and securing structure attached to the strap for securing the strap.

This patent describes a tourniquet system having a strap that may be useful around the legs and aims but would be of no use on the major arteries of the torso.

U.S. Pat. No. 8,834,517 of Croushorn et al. describes a portable pneumatic abdominal aortic tourniquet for occlusion of the abdominal descending aorta to restrict blood supply to a non-compressible arterial hemorrhage in the abdominal region. The tourniquet comprising an adjustable waist strap for securing around an abdomen; a directed air bladder mounted to the waist strap having a generally "V" shaped construction operable between a deflated condition wherein the directed air bladder is collapsed, and an inflated condition wherein the directed air bladder is expanded for exerting pressure against the abdomen; and, an air source connected to the directed air bladder for operating the directed air bladder between the deflated condition and the inflated condition. This device is not suited for application on the upper torso or subclavian area.

This patent describes a portable pneumatic abdominal aortic tourniquet for occlusion of the abdominal descending aorta with arterial hemorrhage in the abdominal region. This patent does not supply a kit with items that will be useful in a variety of different areas of the body. Within tins device also exists the possibility of a fatal flaw, in that this device is made from rubber or the like. As rubber and some similar materials age, they can become brittle and susceptible to cracking, leaking and breaking.

U.S. Pat. No. 9,149,280 of Croushorn et al. describes a portable pneumatic abdominal aortic tourniquet for occlusion of the abdominal descending aorta to restrict blood supply to a non-compressible arterial hemorrhage in or below the inguinal region is presented. The tourniquet includes an adjustable waist strap for securing it around the abdomen of a patient and a windlass rod connected to the waist strap to selectively tighten the strap as needed to tightly secure it to patient. A directed air bladder is mounted to the waist strap having a generally "V" shaped construction and is expanded for exerting directed pressure against the abdomen. Upon inflation of the air bladder and adjustment of the windlass, occlusion or restriction of blood flow through the abdominal descending aorta will occur which will achieve cessation of hemorrhage in or below the inguinal area or achieve other therapeutic effects like elevated blood pressure to enhance CPR or blood flow control to the lower extremities.

This patent still does not supply a kit with items that will be useful in a variety of different areas of the body to restrict blood flow.

U.S. pending patent application Publication No. 20070005107 of John Janota describes a military emergency tourniquet is a device for rapidly and easily reducing or stopping blood flow to a limb. The tourniquet utilizes a closed loop system and includes a twistable strap, a base including two opposing entry apertures and an exit aperture, a windlass and at least one receiving loop. The twistable strap is slidably positioned through the opposing entry apertures and the exit aperture thereby forming a closed loop. The windlass is positioned outside of the closed loop and is affixed to one end of the strap. The windlass includes an aperture capable of sliding the opposing end of the strap there through. The receiving loop receives an end of the windlass and is affixed to the base. This device would require a substantial length of limb to be protruding from torso to function. Therefore, it would be of no use in cases of complete limb amputations.

This patent describes a military emergency tourniquet which is a device for rapidly and easily reducing or stopping blood flow to a limb. The tourniquet utilizes a closed loop system and includes a twistable strap but does not supply a variable height adjustable compression device suitable for application on various parts of the body including the torso. Thus, as mentioned, a disadvantage of this device would be that it would be of no use in cases involving complete amputations.

U.S. pending patent application Publication No. 20130267994AL of Tyler L. Crowder describes an occlusion attachment device for coupling with a tourniquet includes a projection that can be attached using a platform to a portion of a tourniquet in an emergency situation, thereby providing a modified tourniquet that includes the projection. Clip-on, slide-on, and clamping structures associated with the platform are described.

This patent describes an occlusion attachment device for coupling with a tourniquet suitable for an arm or a leg but does not supply a Point Specific Junctional Tourniquet suitable for application on various parts of the body including the torso.

U.S. Pat. No. 8,888,807 of Mark Esposito describes a tourniquet for restricting a flow of blood in a body part is presented. In accordance with embodiments of the present invention, the tourniquet comprises a first elongated member, and a second elongated member in slidable engagement with the first elongated member. In addition, the tourniquet includes a tensioning mechanism connected to the second elongated member, wherein a compressive force is applied to the body part upon applying a tensile force to the second elongated member using the tensioning mechanism. The tourniquet is suited for emergency use and may be applied by using only one hand. Thus, the tourniquet may be applied, manipulated and tightened by the wearer, even if the wearer is limited to the use of a single hand.

This patent describes a tourniquet for restricting a flow of blood in a leg or arm but does not does not supply a tourniquet with variable height compression devices useful in a variety of different areas of the body, but would be of no use in complete dismemberments.

U.S. Pat. No. 8,926,536 of Lance David Hopman et al describes a junctional and truncal tourniquet and a hip-girdling pelvic sling device for maintaining a desired amount of tension surrounding a person's hips and pelvis to securely support and stabilize a pelvis that has been fractured and for securing a pressure applying device to a person with a preferred amount of tension so that blood vessel-occluding pressure can be applied. Areas of mating types of fastener material such as mating hook-beating fastener material and loop pile fastener material are arranged on the device to enable a strap to be secured at various effective lengths to provide a wide range of adjustability. The device may include inflatable bladders, and may be wrapped around a patient's torso to occlude blood vessels proximal to an injury on a limb. A bladder may be expandable in distinct tiers and may carry a separate and removable pressure-concentrating fitting. An auxiliary strap may be included and may be used to keep the junctional and truncal tourniquet in place on a patient's torso. This device also requires an existing limb be present to function.

This patent describes a junctional and truncal tourniquet and a hip-girdling pelvic sling device'for maintaining a desired amount of tension surrounding a person's hips and pelvis to securely support and stabilize a pelvis that has been fractured but does not supply a variable height adjustable compression device tourniquet with features that will be useful in variety of different areas of the body to rapidly restrict blood flow.

SUMMARY OF THE INVENTION

In this respect, before explaining at least one embodiment of the Point Specific Junctional Tourniquet in detail it is to be understood that it is not limited in its application to the details of construction and to the arrangement of the components set forth in the following description or illustrated in the drawings. The Point Specific Junctional Tourniquet is capable of other embodiments and of being practiced and carried out in various ways. Also, it is to be understood that the phraseology and terminology employed herein are for the purpose of description and should not be regarded as limiting.

The Point Specific Junctional Tourniquet is advantageous in that it includes a variable height adjustable point specific tourniquet compression device within small multipurpose kit having a related smartphone application (app) that can be used by any first responders, and the military, as well as civilian medical caregivers.

Another advantage of the Point Specific Junctional Tourniquet is that the variable height adjustable point specific tourniquet compression device can be used with varying compression surface configurations, at various locations on the torso as well as on the arms and legs of a victim.

Another advantage is to create separate parts of the Point Specific Junctional Tourniquet for use on specific locations prone to injury on the body of a victim.

Another advantage is to provide a Point Specific Junctional Tourniquet with a belt including a medical clasp that can be used in varying lengths and varying compression pressures.

Another advantage of the Point Specific Junctional Tourniquet is having the smartphone app which will dial 9-1-1 and then guide the user in proper tourniquet operation in an emergency situation event.

Another advantage of the Point Specific Junctional Tourniquet is the tourniquet belt can have a variety of compression devices including belt attachable, shock cord loops, and height adjustable variable point specific compression point devices.

And still another advantage of the Point Specific Junctional Tourniquet is an alternate embodiment of the tourniquet will include a rotational support member with inclination stops for variable height adjustment of the compression device.

A further advantage Specific Junctional Tourniquet of the tourniquet compression devices be easily and readily attachable to the compression belt, and that belt can be used in various other applications like a personal restraining belt, and a drag strap to quickly move the wounded out of harm's way.

These together with other objects of the Point Specific Junctional Tourniquet, along with the various features of novelty, which characterize the kit, are pointed out with particularity in the claims annexed to and forming a part of this disclosure. For a better understanding of the Point Specific Junctional Tourniquet, its operating advantages and the specific objects attained by its uses, reference should be made to the accompanying drawings and descriptive matter in which illustrate the preferred the embodiments.

The Point Specific Junctional Tourniquet consist of a tourniquet compression cam, tourniquet belt, a variable height adjustable point specific tourniquet compression device which readily couples with a tourniquet belt, wherein the belt has a medical clasp for applying pressure and holding that pressure directly on the specific point of injury.

Though the Point Specific Junctional Tourniquet has been designed as "point specific" it can also be used to apply pressure over an occlusive dressing applied to the shoulder or at the hip in case of full arm and leg amputations. When used to apply pressure to occlusive dressings, a second tourniquet is required since the first tourniquet applied would be applying pressure to the appropriate point on an artery. The application of a secondary device does not present a logistical problem since the victim and care givers will each have their own kits and all kits contents are interchangeable. This Point Specific Junctional Tourniquet can also be used to secure an occlusive dressing virtually anywhere on the torso as its length allows it to be wrapped completely amend the torso. The Point Specific Junctional Tourniquet can also be used to restrain combative casualties as is sometimes necessary in victims with severe brain injuries. This feature is also highly desirable when non-traditional vehicles are used for medical evacuations. When used as a drag/rescue strap the caregivers benefit by being able to walk/run more upright than if they were dragging the victim by the handles on the victim's plate carrier or by the boots since both means require the care giver to bend at the knees and hips.

The tourniquet cam can apply up to 4" of compression, and more if augmented. The kit allows for operator improvisations to facilitate off label applications where deemed necessary to facilitate situation specifics. The tourniquet cam is designed so that it can be used for a straight flat pull making it ideal for use as a litter strap. It can be easily coupled to additional tourniquets if the need should arise.

This Point Specific Junctional Tourniquet can be deployed and in place in less than 30+/− seconds, and readjusted in less. It can be applied without rolling the victim around to apply it. One end is simply pushed halfway under the victim by the caregiver(s) and then pulled out the opposite side to the desired position. The tourniquet's ends are joined at the cam coupling. The variable height adjustable point specific tourniquet compression device is positioned over arteries, at compressible sites, and the belt coupled then pulled to the proper pressure (depth) and held down in place by the medical clasp. Multiple devices can be stacked over each other without conflict as would be the case in double amputations of arms and legs. There is nothing protruding from the tourniquet that can cause it to be dislodged or disrupted.

The Point Specific Junctional. Tourniquet can accommodate torso diameters as small as 28 inches and as large as 60 inches.

The Point Specific Junctional Tourniquet is light in weight and will weigh in at approximately 12 to 32 ounces. It will be economical and available at a price far lower than the ones currently being sold. It is low cube and will fit in a pack with inside dimensions of 5" Depth×6" Width×9" Height and will be available with a container meeting USAMRMC specifications.

The heart of the Point Specific Junctional Tourniquet is the variable height adjustable point specific tourniquet compression device assembly. The tourniquet belt is coupled to the compression device by placing the belt within a strap guide on the bottom of the compression device. It is expected that this Point Specific Junctional Tourniquet component has an indefinite shelf life. It can be expected that military personnel will continue to encounter land mines and IED's that have been randomly scattered in unstable countries as well and that pose a definite threat to their well-being.

Since the detonation of mines, and IEDs, frequently involve multiple casualties and amputations it is recommended that all military personnel, in theaters of operation, have a Point Specific Junctional Tourniquet Kit in addition to their IFAK. Forward combat medical personnel will then have their own kit, as well as the casualty's kit, resulting in the medical corpsman equipped to deal with double extremity amputations.

First responders and civilian law enforcement would also benefit by having their officers and personnel carry Point Specific Junctional Tourniquet for situations like the Boston Marathon (explosion) attacks, mass shootings and mass transit, train, aircraft and vessel crashes.

With respect to the above description then, it is to be realized that the optimum dimensional relationships for the parts of the Point Specific Junctional Tourniquet, to include variations in size, materials, shape, form, function and manner of operation, assembly and use, are deemed readily apparent and, obvious to one skilled in the art, and all equivalent relationships to those illustrated in the drawings and described in the specification are intended to be encompassed by the present design. Therefore, the foregoing is considered as illustrative only of the principles of the Junctional Tourniquet. Further, since numerous modifications and changes will readily occur to those skilled in the art, it is not desired to limit the design to the exact construction and operation shown and described, and accordingly, all suitable modifications and equivalents may be resorted to, falling within the scope of the invention.

BRIEF DESCRIPTION OF THE DRAWINGS

The accompanying drawings, which are incorporated in and form a part of this specification, illustrate embodiments of the Point Specific Junctional Tourniquet and together with the description, serve to explain the principles of this application.

FIG. 8 depicts a segment of the tourniquet belt with hook sections on either side and a loop section down the center.

FIG. 9 depicts a segment of the tourniquet belt with loop sections on both sides and hook section down the center.

FIG. 10 depicts a segment of the tourniquet belt with hook and loop segments on an angle.

FIG. 11 depicts a segment of the tourniquet belt with plurality of grommets on the full length.

FIG. 12 depicts a perspective view of an alternate embodiment of a tourniquet belt with a plurality of grommets on the full length and a specialized belt buckle.

FIG. 21 depicts an assembled rotational variable height adjustable point specific compression device.

FIG. 22 depicts an exploded view of a disassembled rotational variable height adjustable point specific compression device, illustrating the inclination stops and the inclination stop mating surfaces.

The Junctional Tourniquet Kit consist of a tourniquet compression cam, tourniquet belt, a pressure coupler plate, a horizontal utility device, a contoured utility device, an iliac pressure device, an axillary pressure device, and a pair of utility support straps. The junctional Tourniquet Kit will all be housed within a fabric pouch with a lanyard to thread the separate parts on keeping them together but easily accessible.

DETAILED DESCRIPTION OF THE PREFERRED EMBODIMENTS

Figure 1:
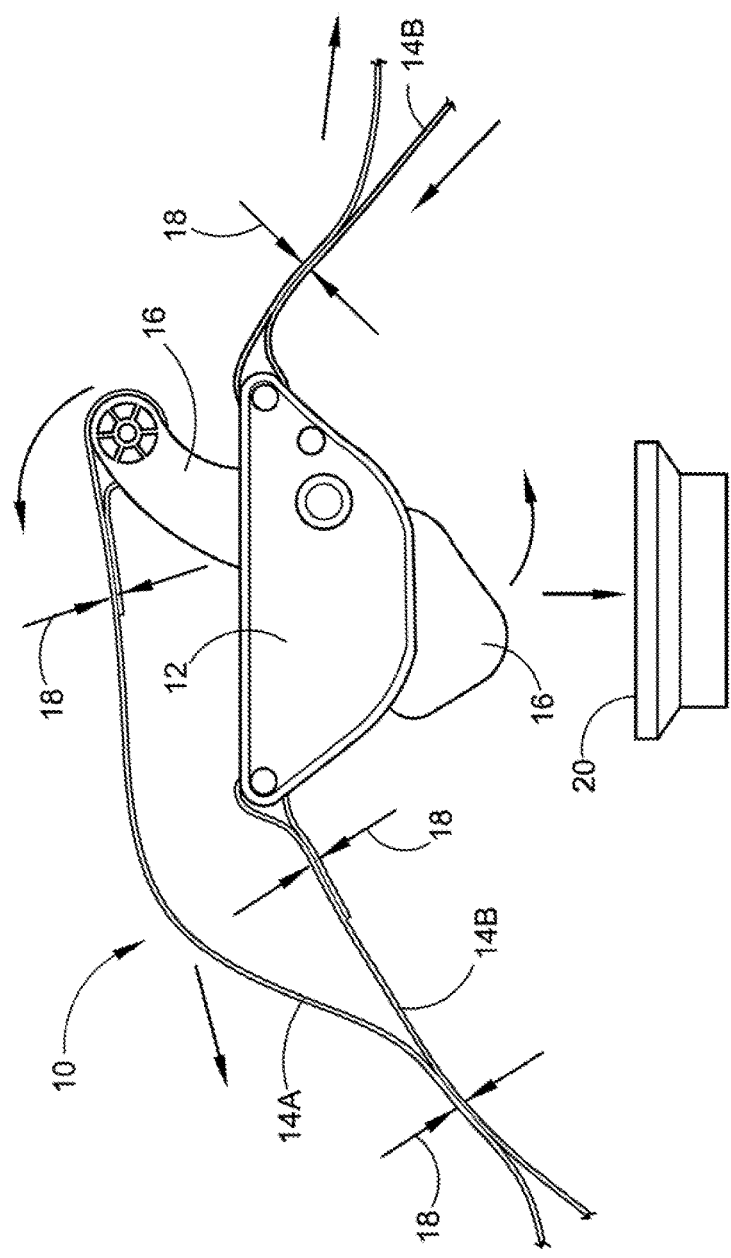
FIG. 1 a front view of the major components of the Point Specific Junctional Tourniquet.

Referring now to the drawings, wherein similar parts of the Junctional Tourniquet. Kit 10 identified by like reference numerals, there is seen in FIG. 1 a front view of some of the components of the Junctional Tourniquet Kit 10 and the actions of the tourniquet compression cam 12 along with the associated parts of the kit. The tourniquet compression cam 112 can be used as a compression device to restrict the flow of blood through an artery or it can be used as a means to tighten the tourniquet belt 14A into a desired position.

The tourniquet compression cam 12 is shown with a short section of the tourniquet belt 14A attached around the upper section of the cam lever 16 by a hook-loop attachment means 18. A long section of the tourniquet belt 14B is attached around the left side of the. tourniquet compression cam 12 by a second hook-loop attachment means 18 to be extended around the person and pulled tight to the right side of the tourniquet compression cam 12 and secured to it by a third hook-loop attachment means 18. The short section of the tourniquet belt 14A is then pulled, rotating the upper section of the cam lever arm 16 and extending the lower section of the cam lever 16 downward. The Short section of the tourniquet belt 14A is then secured to the long section of the tourniquet belt 1413 by the fourth book-loop attachment means 18. The belts 14A and 148 will have a hook-loop attachment means 18 on both sides.

The pressure coupler plate 20 is shown below the tourniquet compression cam 12 to be attached to the horizontal utility point specific pressure device 22, or the contoured utility point specific pressure device 24, or the iliac point specific pressure device 26 when a specific tourniquet application is needed.

Figure 2:
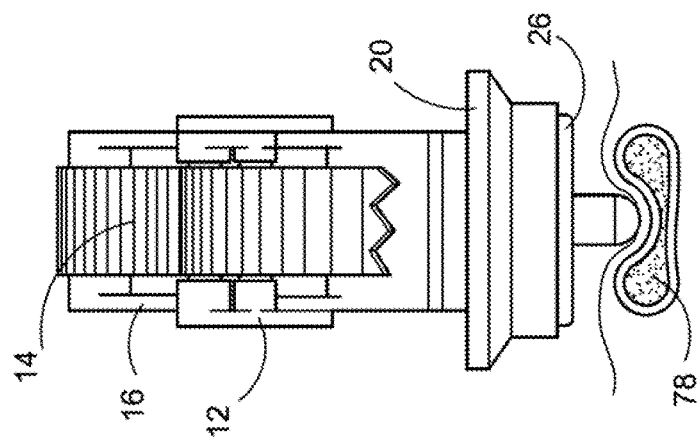
FIG. 2 depicts an end view of the tourniquet compression cam and belt pressing down on the pressure coupler plate and the horizontal utility device compressing a typical artery.

FIG. 2 depicts an end view of the tourniquet compression cam 12 and tourniquet belt pressing down on the pressure coupler plate 20 and the horizontal utility device compressing a typical artery.

Figure 3:
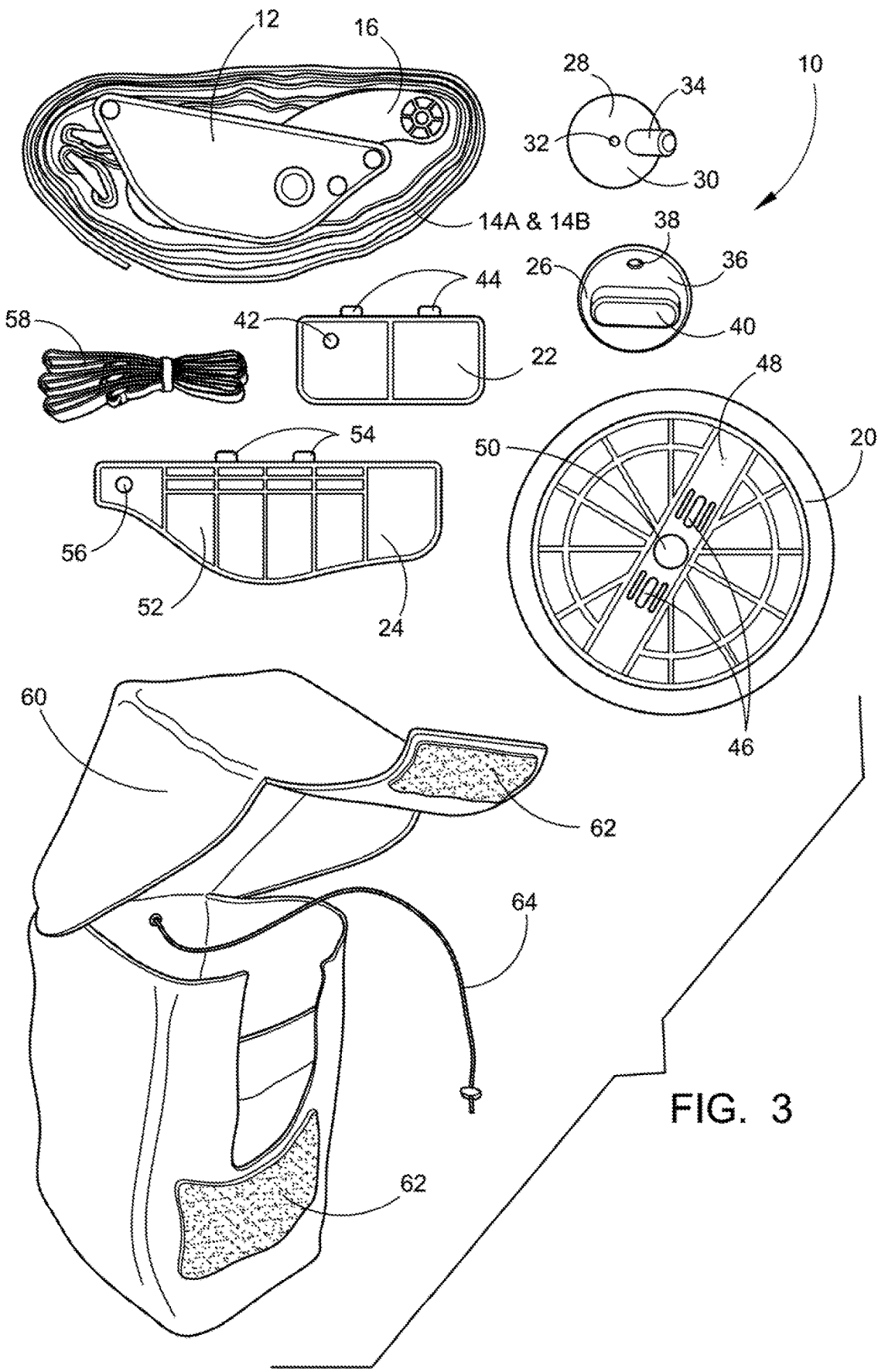
FIG. 3 depicts all of the components of the Point Specific junctional Tourniquet assembled into a kit.

FIG. 3 depicts all of the components of the Junctional Tourniquet Kit 10 including the tourniquet compression cam 12 having a cam lever 16, the tourniquet belt 14A and 14B, the axillary device 28 with a flat base 30, a lanyard orifice 32, and pinpoint angled dowel 34 for centralized pressure positioning. Additional parts to the kit include the iliac pressure device 26 having a flat base 36, a lanyard orifice 38 and an elongated pressure section 40. A horizontal utility device 22 with a lanyard orifice 42 has two key elements 44 that locate within orifices 46 in the alignment track 48 on the pressure coupler plate 20. The pressure coupler plate 20 has a central lanyard orifice 50. The contoured utility device 52 with the two key elements 54 that locate within orifices 46 in the alignment track 48 on the pressure coupler plate 20 and a lanyard orifice 56. The contoured utility device 52 has been designed to fit into the variety of contours in the hip area. A set of utility support or restraint straps 58 are included within the kit. The complete Junctional Tourniquet Kit 10 will fit into the fabric kit bag 60 having the hook-loop closure sections 62 and the attached lanyard 64. This specific point junctional tourniquet kit is expandable in that components of one can be added to another to address numerous unique issues when encountered in the field.

Figure 4:
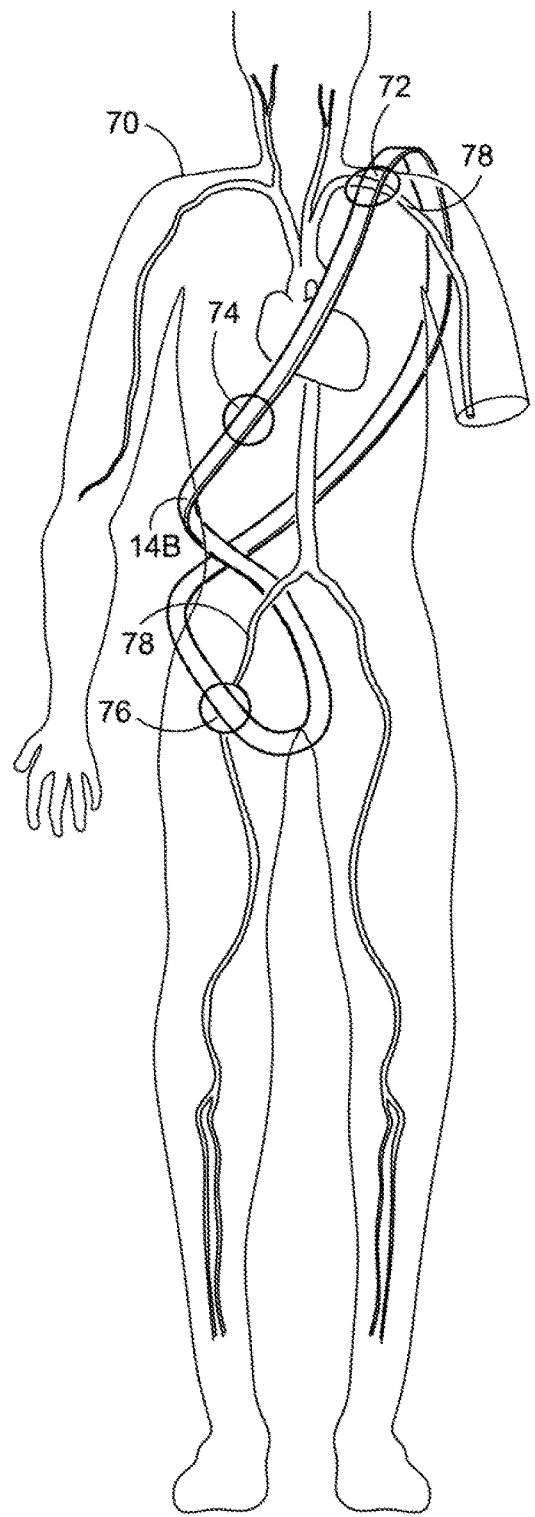
FIG. 4 depicts a silhouette of a person with the tourniquet belt wrapped around indicating some the locations that the pressure may be applied on the major arteries on one side of the body.

FIG. 4 depicts a silhouette of a person 70 with the tourniquet belt 14B wrapped around indicating some the pressure locations 72, 74 and 76 that the pressure may be applied on the major arteries 78 on one side of the body. The tourniquet belt strap could also be used to fashion/fabricate an improvised splint, and maybe even a soft cast as a result of the configuration of the hook and loop sewn onto the strap.

Figure 5:
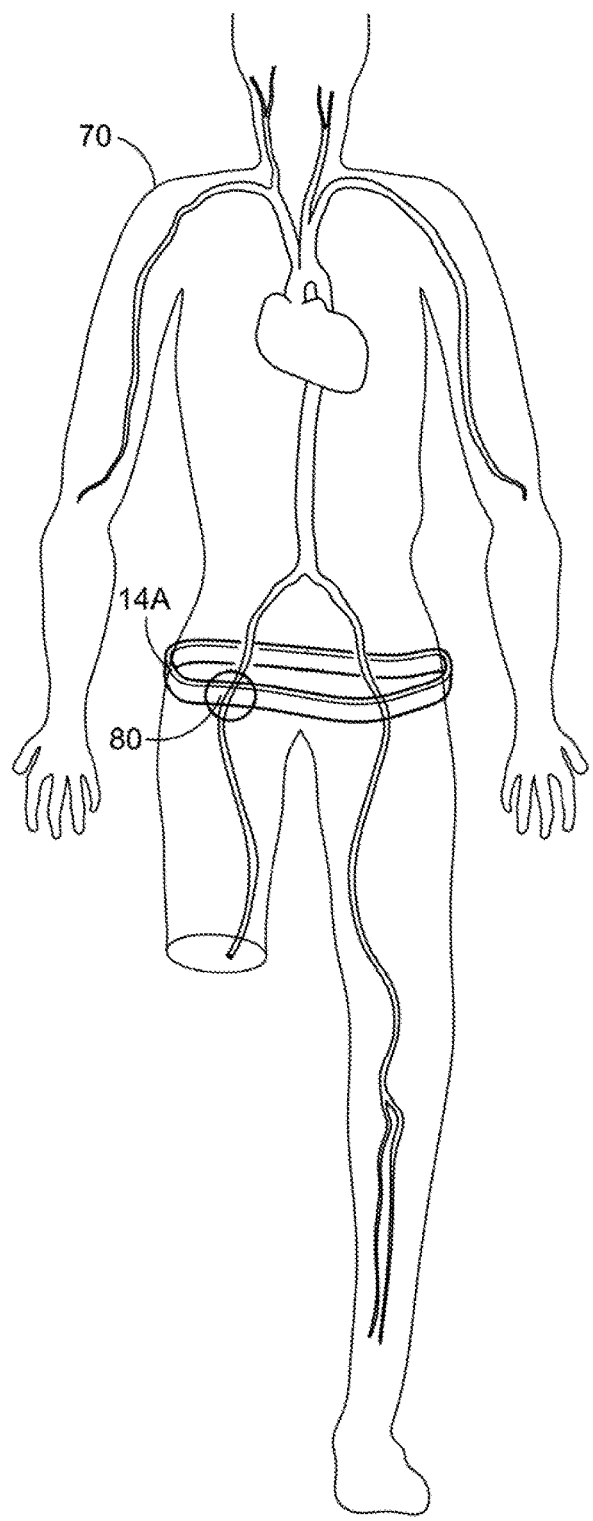
FIG. 5 depicts a silhouette of a person with the tourniquet belt wrapped around the lower waist of the person.

FIG. 5 depicts a silhouette of a person 70 with the tourniquet belt 14A wrapped around the lower waist of the person indicating a pressure location 80 on one side of the body. This tourniquet belt 14A could also be used to stabilize flailed chests, flailed hips and or flailed shoulders if necessary.

Figures 6, 7:
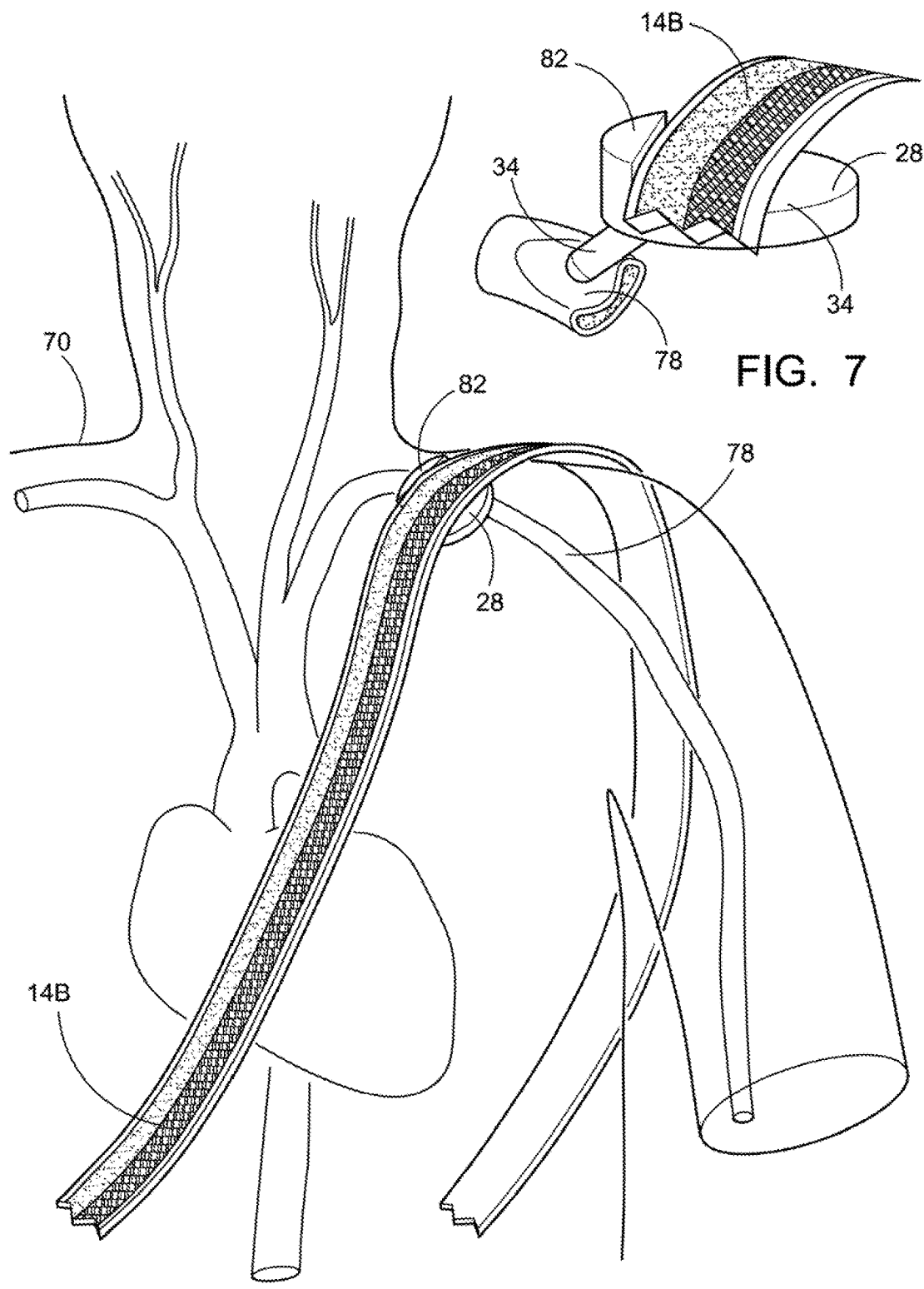
FIG. 6 depicts an enlarged silhouette of the shoulder area with the tourniquet belt going over the axillary pressure device.
FIG. 7 depicts a perspective illustration of the tourniquet belt over the axillary pressure device putting pressure on an artery.

FIG. 6 depicts an enlarged silhouette of the shoulder area of a person 70 with the tourniquet belt 14B having a strip of hook material, and a strip of loop material together going over the axillary pressure device 28 with the retainer edge 82 keeping the tourniquet belt 14B in position. With the strips of hook material and loop material on both sides of the tourniquet belt 14B the belt can be turned over to secure it together into position. In this application the tourniquet compression cam 12 could be used as a means to tighten the tourniquet belt 14B into the desired location.

FIG. 7 depicts a perspective illustration of the tourniquet belt 14B over the axillar pressure device 28 with the angled dowel 34 putting direct pressure on a major artery 78 with the tourniquet belt 14B held in position by the means of the retainer edge 82.

FIG. 8 depicts a segment of the tourniquet belt 14C with hook sections on the outside and loop section down the center.

FIG. 9 depicts a segment of the tourniquet belt 14D with loop sections on the outside and hook sections down the center.

FIG. 10 depicts a segment of the tourniquet belt 14E with hook and loop segments on an angle.

FIG. 11 depicts a segment of the tourniquet belt 14F with plurality of grommets 88 on the length.

FIG. 12 depicts a perspective view of an alternate embodiment of a tourniquet belt 14F with a plurality of grommets 88 on the full length and a specialized belt buckle 90.

Figure 13:
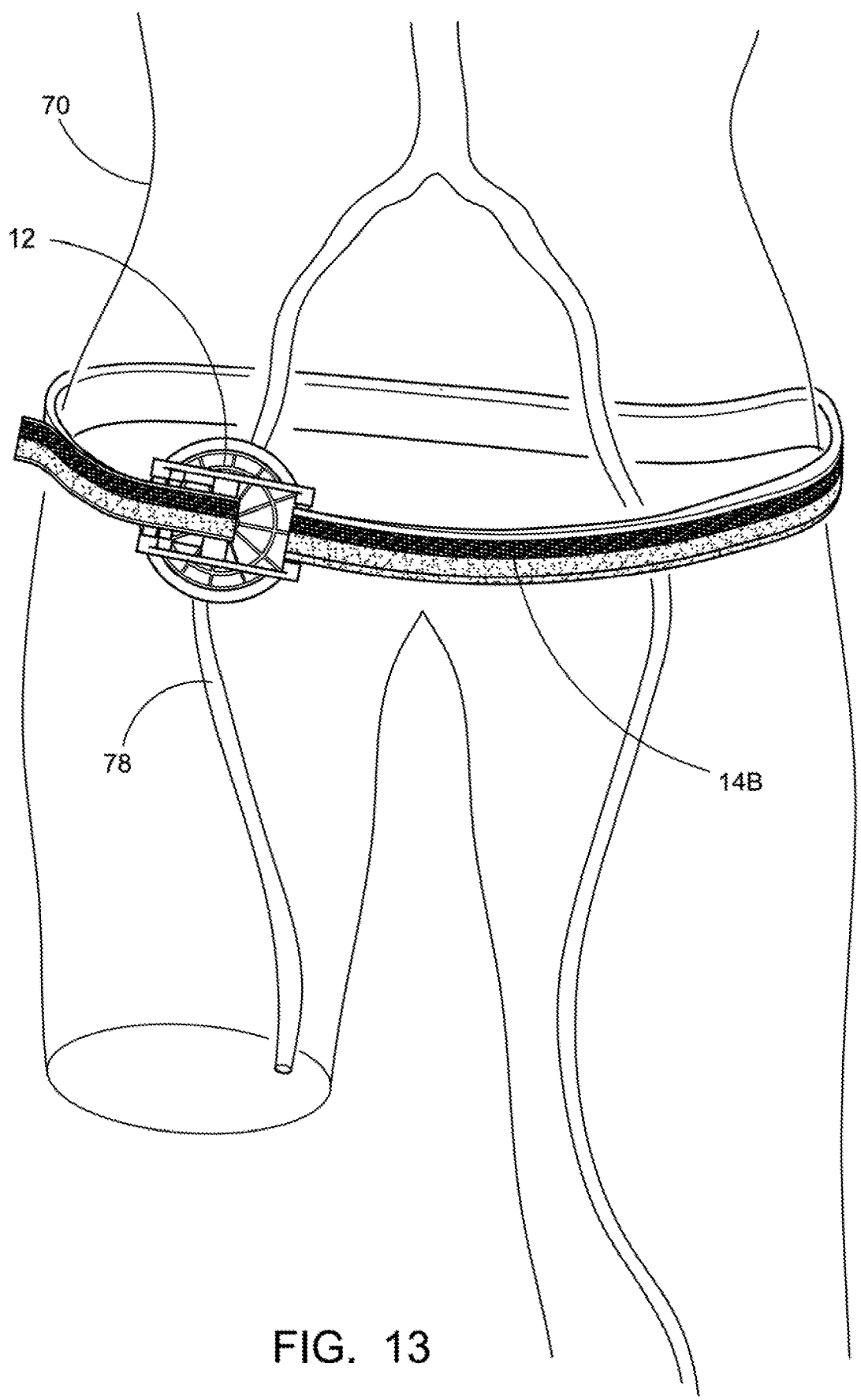
FIG. 13 depicts a silhouette of the lower portion of a person with the tourniquet compression cam and tourniquet belt putting pressure on the right iliac artery.

FIG. 13 depicts a silhouette of the lower portion of a person 70 with the tourniquet compression cam 12 and tourniquet belt 14B putting pressure on the major artery 78.

Figure 14:
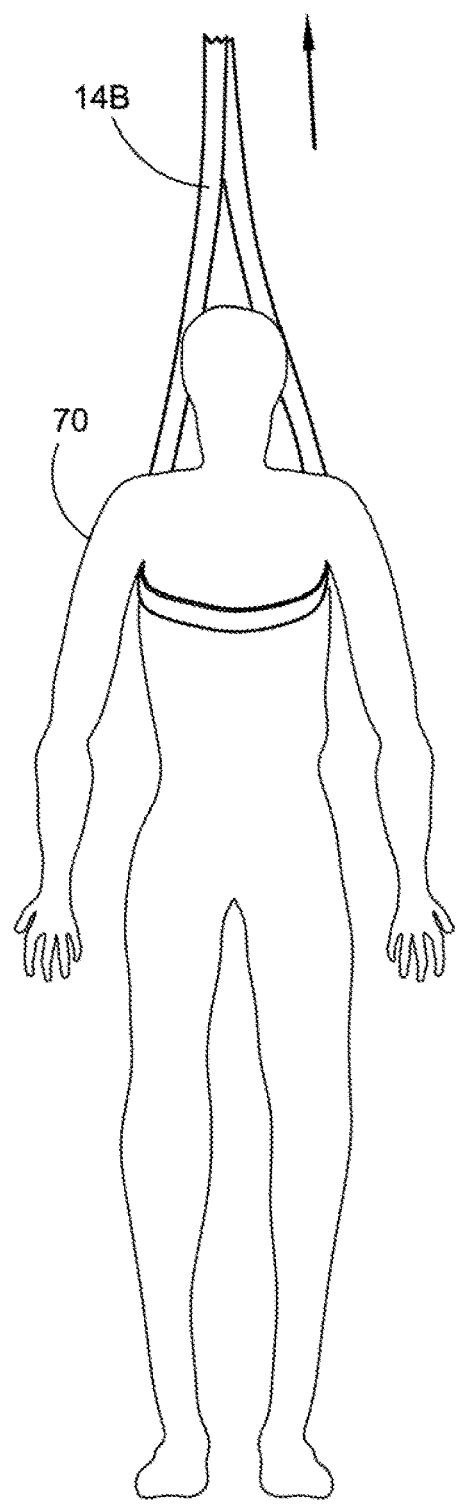
FIG. 14 depicts silhouette of a person with the tourniquet belt being used as a drag strap under the arms.

FIG. 14 depicts silhouette of a person 70 with the tourniquet belt 14B being used as a drag strap under the arms.

Figure 15:
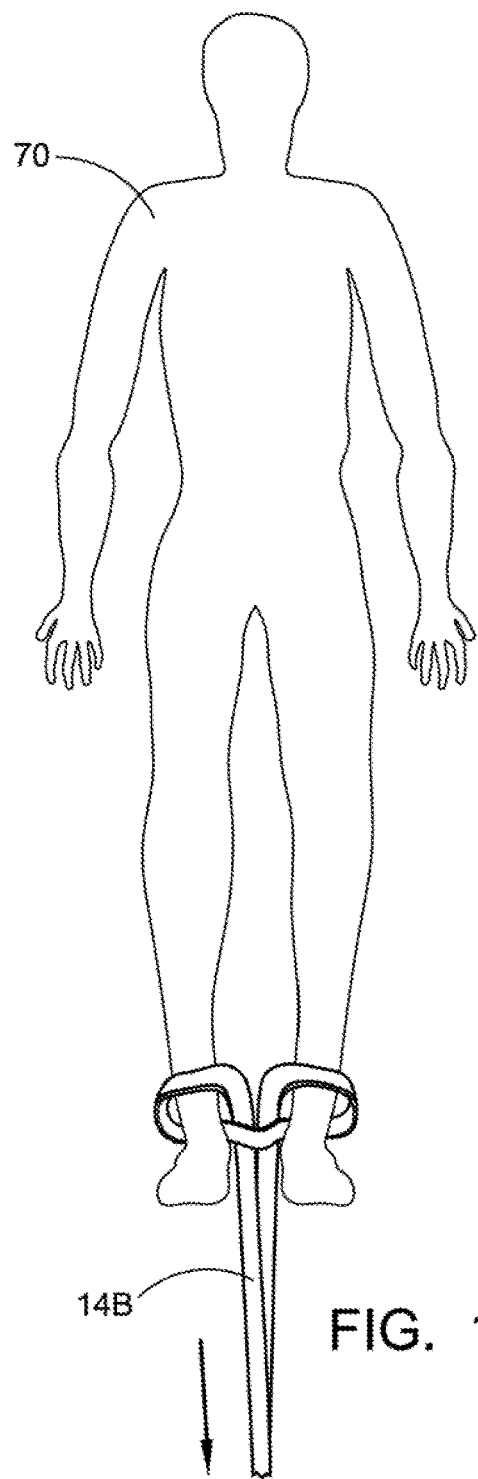
FIG. 15 depicts silhouette of a person with the tourniquet belt being used as a drag strap around the ankles.

FIG. 15 depicts silhouette person 70 with the tourniquet belt 14B being used as a drag strap around the ankles.

Figure 16:
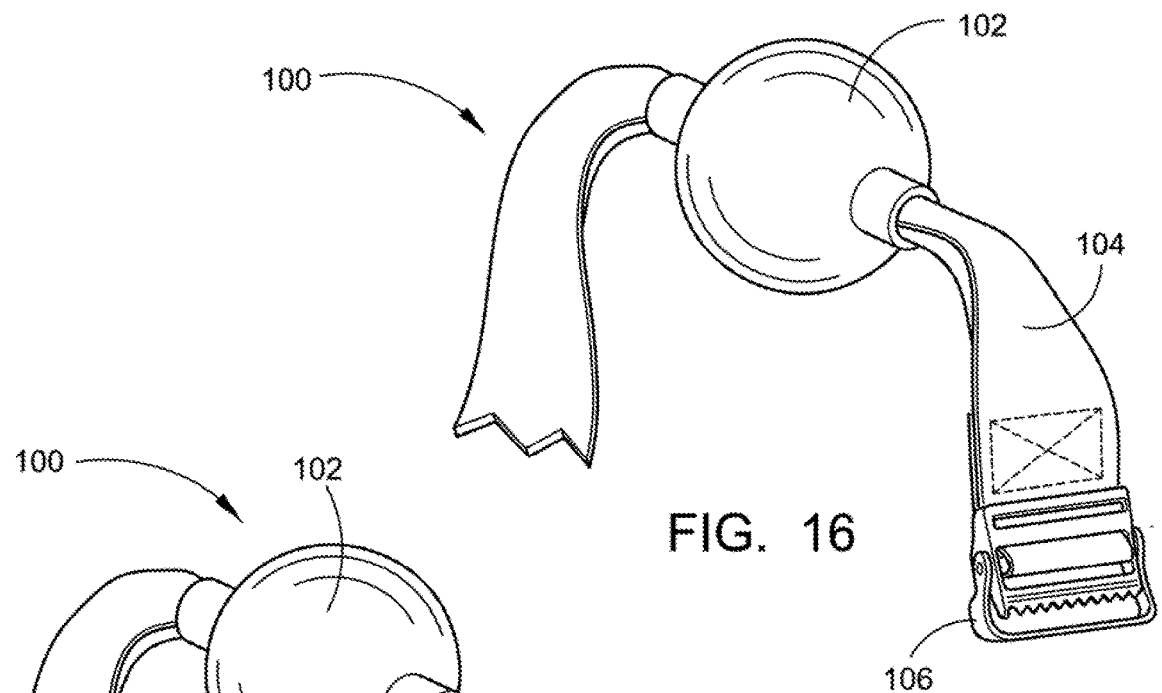
FIG. 16 depicts a spherical ball compression device mounted on a tourniquet belt having a medical clasp.

FIG. 16 depicts a tourniquet 100 having a spherical ball compression device 102 mounted on a tourniquet belt 104 having a medical clasp 106. The spherical ball compression device .102 includes a hollow channel for threading the belt 104 through it, and in this way differing compression devices, depending upon application and victim wound or injury type, can be mounted to the belt 104 and used. After mourning the spherical ball compression device 102 to belt 104 the medical clasp 106 is used to secure and apply pressure to the wound of the victim.

Figure 17:
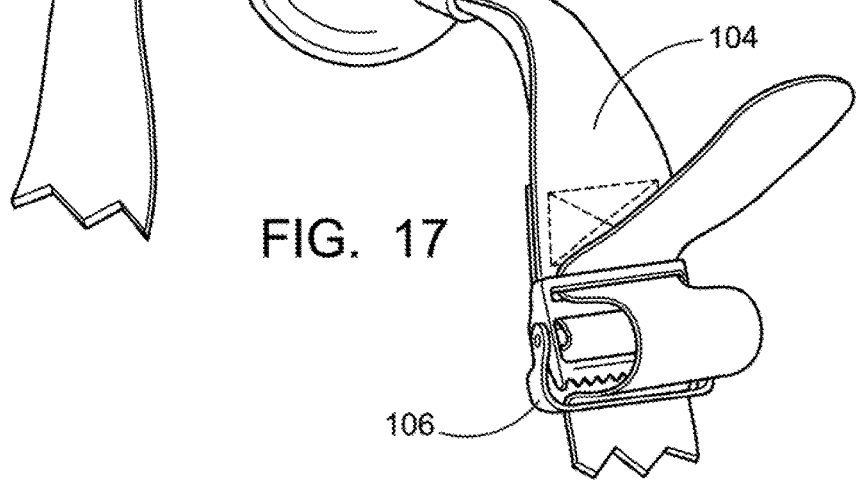
FIG. 17 depicts a spherical ball compression device mounted on a tourniquet belt having a medical clasp illustrating the belt end threaded through the medical clasp.

FIG. 17 depicts a tourniquet 100 having a spherical ball compression device 102 mounted on a tourniquet belt 104 having a medical clasp 106, and illustrating the belt end threaded through the medical clasp 106. The medical clasp 106 mechanism acts to apply pressure and keep pressure on the wound in a secure manner.

Figure 18:
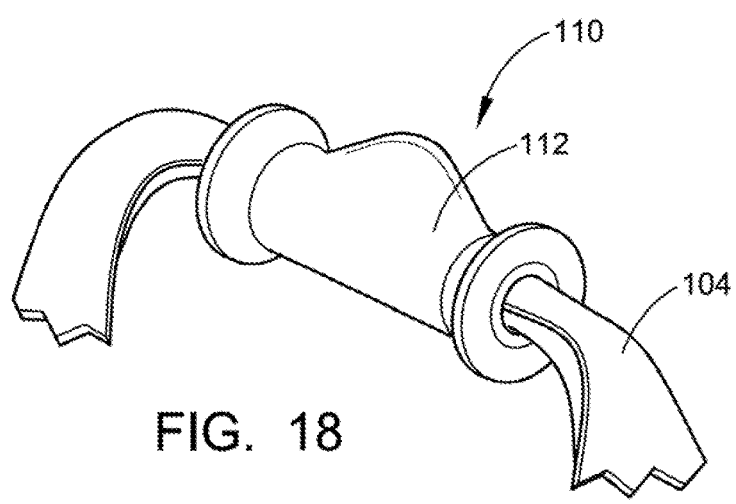
FIG. 18 depicts a small frame handle compression device mounted on a tourniquet belt.

FIG. 18 depicts a tourniquet 110 including a small frame handle compression device 112 mounted on a tourniquet belt 104. The small frame handle compression device 112 includes a hollow channel for threading the belt 104 through it, and in this way differing compression devices, depending upon application and victim wound or injury type, can be mounted to the belt 104 and used. This small frame handle compression device can be applied to smaller adult victims and children.

Figure 19:
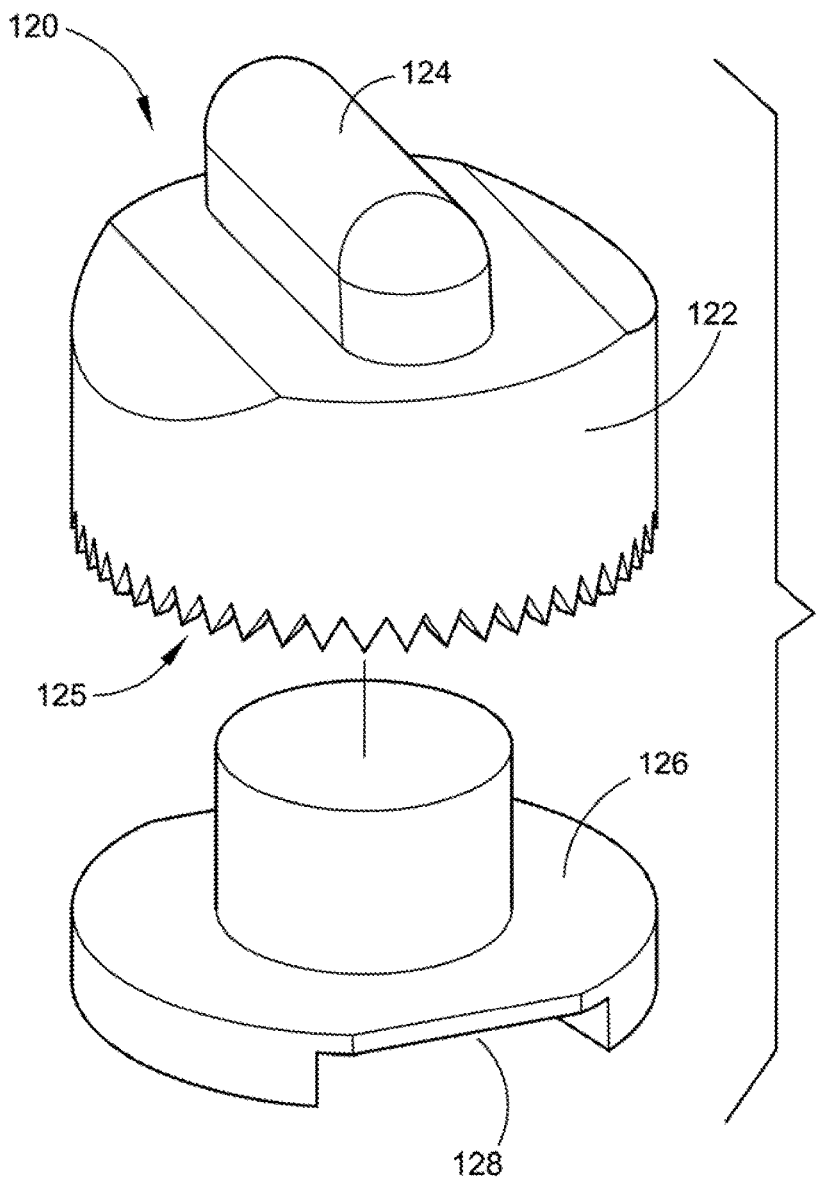
FIG. 19 depicts variable point specific compression device having inclination stops and a belt strap guide on the base.

FIG. 19 depicts an exploded view of a tourniquet component two-piece point specific compression device 120 having a pressure form 124 on top of a housing 122 and belt/strap engaging spikes 125 along the bottom of the housing 122. Located below the housing 122 is a base 126 having an integral belt/strap guide 128. The pressure form 124 can take many shapes and sizes depending on the injury requirement, and it is anticipated that numerous housings 122 having varying pressure forms 124 will be carried in a complete kit of injury/emergency situation event adaptable tourniquets and using the same base 126 will be applied using a strap/belt held in place by the belt/strap guide 128. Additionally, the inclination stops 125 may be used to secure the belt/strap when the pressure form 124 and base 126 is not used with the housing 122 to apply pressure to a wound.

Figure 20:
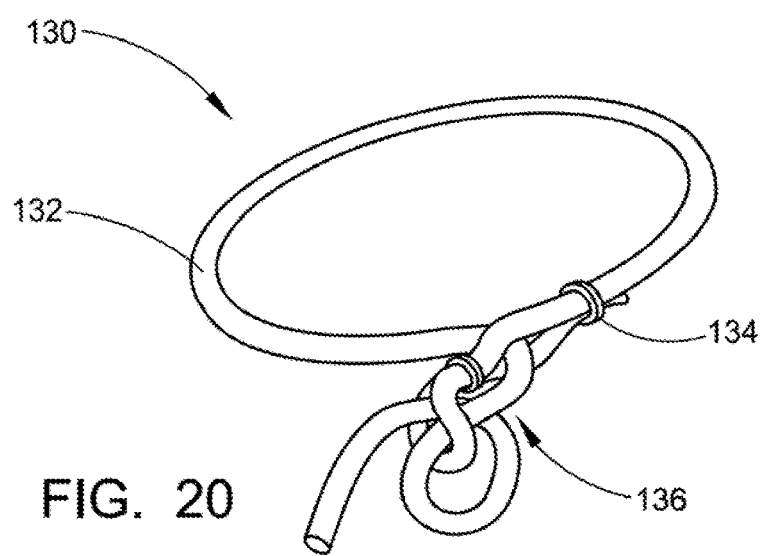
FIG. 20 depicts shock cord tourniquet assembly having an adjustable compression loop knot.

FIG. 20 depicts shock cord tourniquet assembly 130 having an adjustable compression loop knot 136 tied in to a shock cord loop 132 and held together by one or more hog rings 134. This small, simple to use and inexpensive to own type of shock cord tourniquet assembly 130 can be carried in a tourniquet kit and rapidly deployed in an emergency event. The shock cord loop 132 is wrapped around the injury area or injured limb and tightened down using the adjustable compression loop knot 136 to apply and hold pressure on the wound. The result of the shock cord tourniquet assembly 130 design makes it easy to carry, easy to use, quick to deploy and inexpensive to own.

FIG. 21 depicts an assembled rotational variable height adjustable point specific compression device 140. This compression device 140 has a variable pressure form 143 on top of the housing 142. The base 146 has gripping handles 144 and an integral belt/strap guide 148. For height adjustment of the housing 142 and pressure form 143, the user grips the housing 142 and the base gripping handles 144 and twists the housing 142 causing the height of the housing to increase in click stops (see interior mechanism in FIG. 22). After the optimum height is reached, depending upon the injury or wound, the assembled rotational variable height adjustable point specific compression device 140 is secured in place and pressure is applied using the belt/strap held in place within the belt/strap guide 148.

FIG. 22 depicts an exploded view of a disassembled rotational variable height adjustable point specific compression device 140, illustrating the inclination stops 150 and the inclination stop mating surfaces 154 that make height adjustment possible. On the interior of the height adjustment mechanism upper housing 142 there is shown a center post 166 and a spiral configured set of inclination stops 150. The lower housing with gripping handles 144 has a mating center post 164 and inclination mating stops surfaces 154 also in a spiral configuration, which mates with inclination stops 150. The base 146 includes a center hole 162 with tabs located in the center of an index plate 158 which is fitted to with a screw collar 156. The integral belt/strap guide 148 in on the lower surface of the base 146 and the screw access plug 160 fits into the center hole 162 when the unit is assembled. Spring 152 fits ever center post 164 and keeps the assembled unit 140 together as it click stops through the height adjustment when the inclination stops 150 and the inclination mating surface 154 is engaged with the assembled unit 140.

After the optimum height is reached, depending upon the injury or wound, the assembled rotational variable height adjustable point specific compression device 140 is secured in place and pressure is applied using the belts rap held in place within the belt/strap guide 148.

Figure 23:
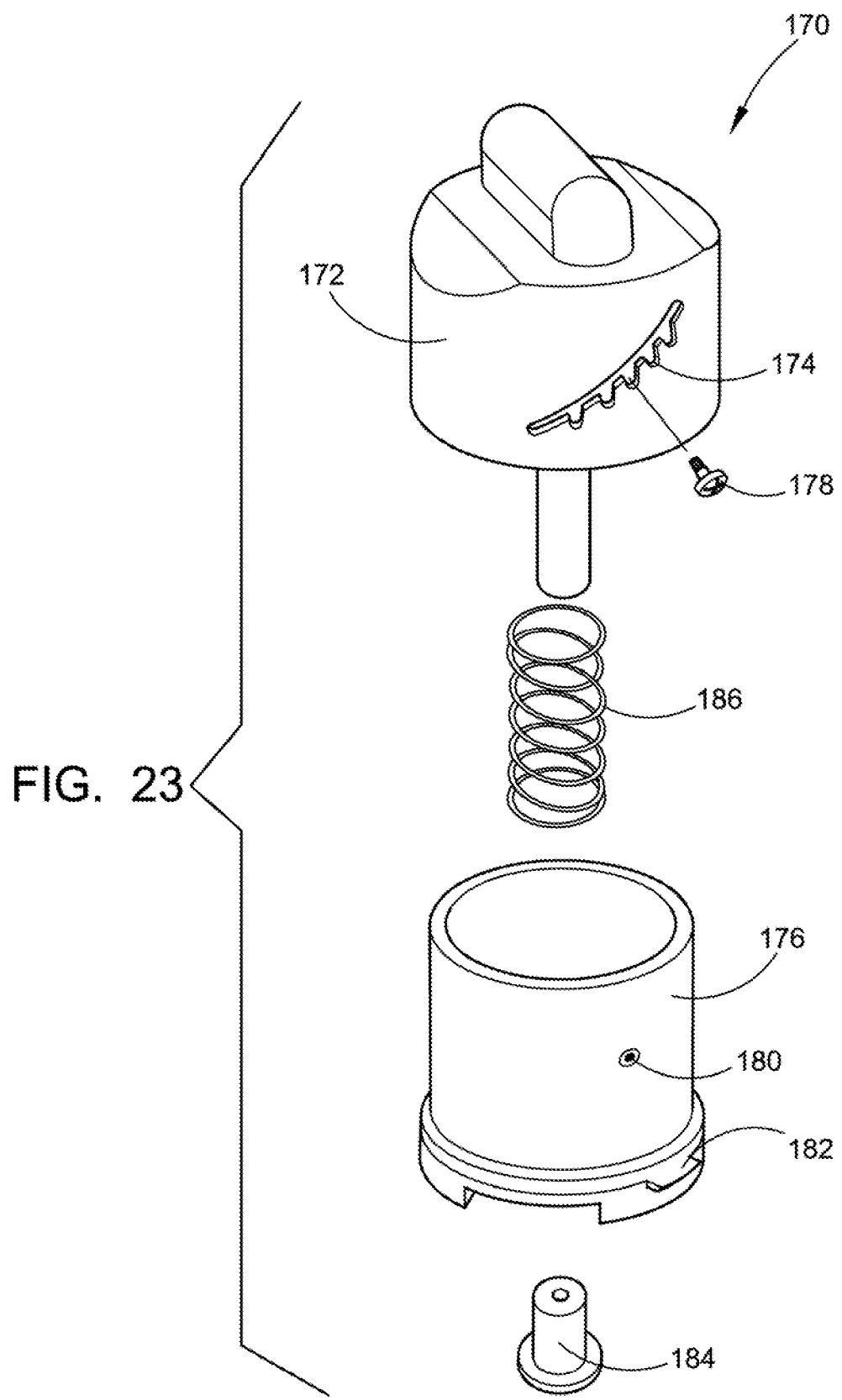
FIG. 23 depicts an exploded view of a disassembled alternate embodiment of the rotational variable height adjustable point specific compression device, illustrating inclination stops located on the housing surface.

FIG. 23 depicts an exploded view of a disassembled alternate embodiment of the rotational variable height adjustable point specific compression device 170, illustrating inclination stop slots 174 located on the exterior of the housing 172 surface. A lower housing 176 has a threaded orifice 180 to accept a set screw 178. The base 182 has handles and a belt/strap guide as in previous embodiments. When assembled, the rotational variable height adjustable point specific compression device 170 upper housing 172 is placed over the lower housing 176 and secured using a screw access plug 184 and spring 186 set on a center post. Set screw 178 is then threaded into threaded orifice 180. When in use, the height is adjusted by rotationally running through the inclination stop slots 174 then securing the optimal height with set screw 176. After the optimum height is reached, depending, upon the injury or wound, the assembled rotational variable height adjustable point specific compression device 170 is secured in place and pressure is applied using the belt/strap held in place within the belt/strap guide.

Figure 24:
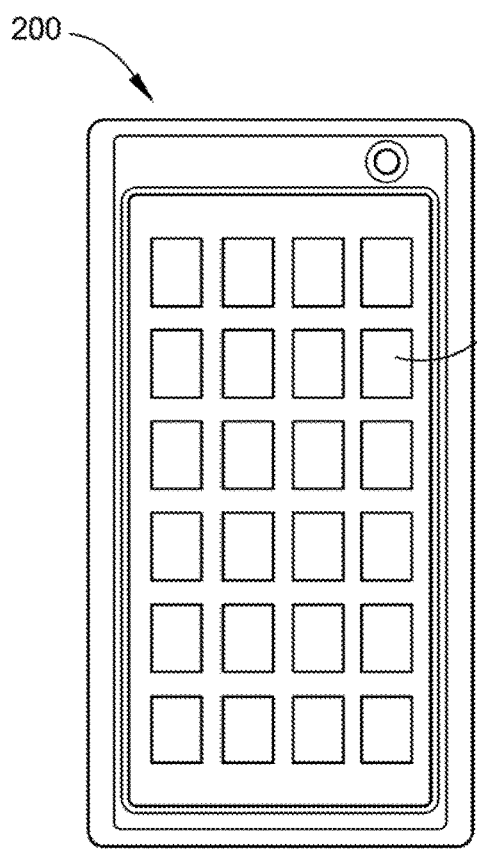
FIG. 24 depicts a smartphone having a normal matrix of smartphone applications icon buttons on its screen, one of which is the First Forward smartphone app icon button.

FIG. 24 depicts a smartphone 200 having a normal matrix of smartphone applications icon buttons on its touch screen, one of which is the First Forward Emergency Tourniquet smartphone app icon button 202. When required, the user touches the First Forward app icon button 202 and this opens the home screen for the First Forward Emergency Tourniquet smartphone app.

Figure 25:
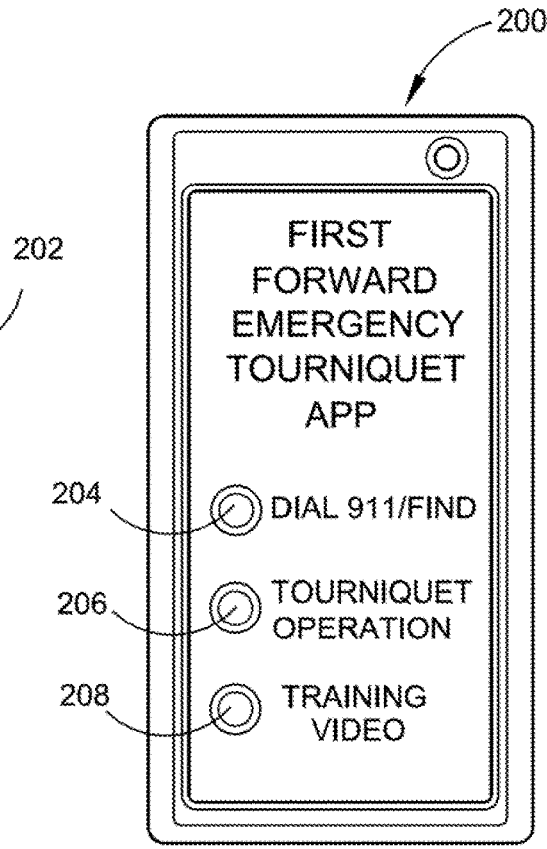
FIG. 25 depicts the home screen of the First Forward emergency tourniquet app.

FIG. 25 depicts a smartphone 200 having the open home screen of the First Forward Emergency Tourniquet app. The home screen includes three or more buttons including a DIAL 911/FIND button 204, a TOURNIQUET OPERATION button 206 and a TRAINING VIDEO button 208. When the DIAL 911/FIND button 204 is touched the smartphone dials 9-1-1 and gives the dispatcher the GPS location of the smartphone. If a cell tower is not available, then when the 911/FIND button 204 is touched a satellite phone GPS locator is activated, and the GPS coordinates are transmitted to the 911 dispatcher. When the TOURNIQUET OPERATION button 206 is touched then the smartphone 200 screen goes to the Tourniquet Operation screen (see FIG. 26). When the TRAINING VIDEO button 208 is touched then the smartphone 200 screen goes to the Training Video screen (see FIG. 27).

Figure 26:
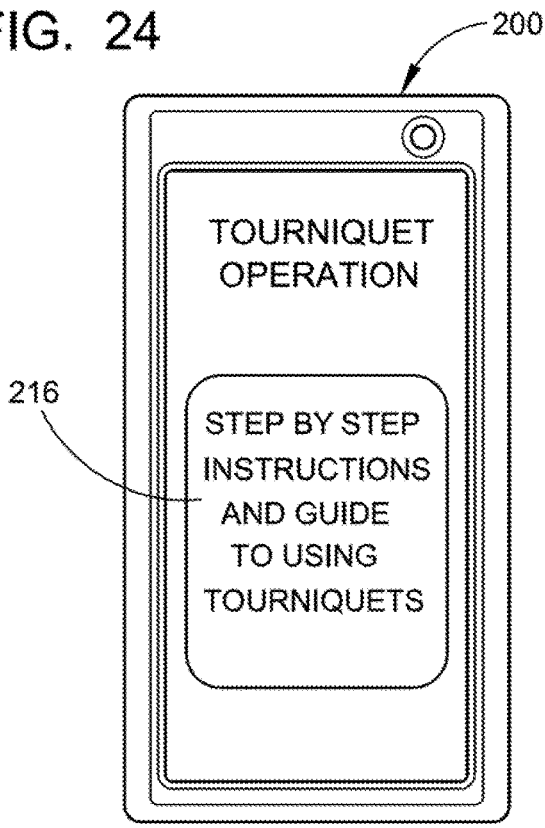
FIG. 26 depicts the tourniquet operations screen of the First Forward emergency tourniquet app.

FIG. 26 depicts the tourniquet operations screen 216 of the First Forward Emergency Tourniquet app 202 on a smartphone 200 screen. When activated by touching, the tourniquet operation button 206 displays a tourniquet operation screen 216 which provides step by step instructions and guide to using the various tourniquets provided by First Forward.

Figure 27:
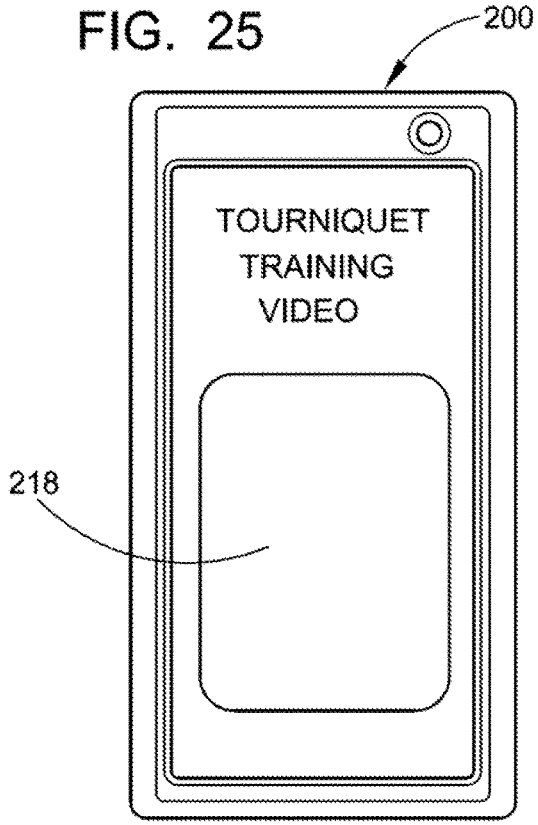
FIG. 27 depicts the tourniquet training video screen of the First Forward emergency tourniquet app.

FIG. 27 depicts the tourniquet training video screen 218 of the First Forward Emergency Tourniquet app 202 on a smartphone 200 screen. When activated by touching, the tourniquet training video button 208 displays a tourniquet training video screen 218 which provides training videos, and audio step by step instructions and a guide to using the various tourniquets provided by First Forward.

The Point Specific Junctional Tourniquet 10 shown in the drawings and described in detail herein disclose arrangements of elements of particular construction and configuration for illustrating preferred embodiments of structure and method of operation of the present design. It is to be understood, however, that elements of different construction and configuration and other arrangements thereof, other than those illustrated and described may be employed for providing a Point Specific Junctional Tourniquet 10 in accordance with the spirit of this application, and such changes, alternations and modifications as would occur to those skilled in the art are considered to be within the scope of this application as broadly defined in the appended claims.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature arid essence of the technical disclosure of the application. The abstract is neither intended to define the Point Specific Junctional Tourniquet of the application, which is measured by the claims, nor is it intended to be limiting as to the scope of the design in any way.

I claim:

1. A point specific junctional tourniquet comprising:
   (a) a rotational variable height adjustable point specific compression device including an upper housing having a top portion wherein a variable pressure form is located on the top portion of said upper housing; and
   b) a lower housing having gripping handles capable of being rotationally nested within said upper housing;
   (c) a base rotationally attachable to said lower housing, said base having an integral belt/strap guide; and
   (c) a belt/strap having a medical clasp for securing said belt/strap in varying lengths to apply varying pressure;
   wherein for height adjustment of said upper housing and pressure form, a user grips the upper housing and the lower housing by the base gripping handles and rotationally twists the two gripped housings causing the overall height of the rotational variable height adjustable point specific compression device upper housing to increase in click stops; and
   further wherein after an operationally desired height is reached, said rotational variable height adjustable point specific compression device is secured in place and pressure is applied using the belt/strap held in place within the belt/strap guide.

2. The point specific junctional tourniquet according to claim 1, wherein said upper housing has a plurality of inclination stops located on a spiraling interior surface wall.

3. The point specific junctional tourniquet according to claim 2, wherein said lower housing further includes a plurality of spiraling mating inclination stops capable of mating with said upper housing plurality of inclination stops.

4. The point specific junctional tourniquet according to claim 3, wherein said lower housing has a center post and is nested into said upper housing having a center post and a spring is placed upon said lower housing and upper housing center post to allow expansion and height adjustment of said rotational variable height adjustable point specific compression device.

5. The point specific junctional tourniquet according to claim 4, wherein said upper housing center post is inserted into said lower housing center post and said upper and lower housings are secured using a screw and screw access plug.

6. The point specific junctional tourniquet according to claim 1, wherein said upper housing further includes belt/strap engaging spikes located along the bottom of the housing.

7. The point specific junctional tourniquet according to claim 1, wherein said rotational variable height adjustable point specific compression device includes:
(a) inclination stop slots located on the upper housing surface;
(b) a set screw; and
wherein when assembled the rotational variable height adjustable point specific compression device upper housing is placed over the lower housing and secured using said set screw;
further wherein said set screw is then threaded into said threaded orifice, and when in use, the overall height of said rotational variable height adjustable point specific compression device is adjusted by rotationally running through the inclination stop slots, then securing an optimal height with said set screw, and after the operationally desired height is reached, the rotational variable height adjustable point specific compression device is secured in place and pressure is applied using the belt/strap held in place within the belt/strap guide.

8. The point specific junctional tourniquet according to claim 7, wherein said upper housing further includes a center post and a spring set on said center post, and a screw access plug.

9. The point specific junctional tourniquet according to claim 1, wherein said rotational variable height adjustable point specific compression device is provided with a smartphone application having a menu system including:
(a) a dial 9-1-1/find button;
(b) a tourniquet operation instructions button; and
(c) a tourniquet training video button;
wherein when in an emergency situation event a user can push the 9-1-1 button to alert authorities and push the tourniquet operation instructions button to follow a step by step set of instructions and guide to using the rotational variable height adjustable point specific compression device provided.

10. A method for making a point specific junctional tourniquet comprising the steps of:
(a) providing a rotational variable height adjustable point specific compression device including an upper housing having a top portion wherein a variable pressure form is located on the top portion of said upper housing; and
(b) providing a lower housing having gripping handles capable of being rotationally nested within said upper housing;
(c) providing a base rotationally attachable to said lower housing, said base having an integral belt/strap guide; and
(c) providing a belt/strap having a medical clasp for securing said belt/strap in varying lengths to apply varying pressure;
wherein for height adjustment of said upper housing and pressure form, a user grips the upper housing and the lower housing by the base gripping handles and rotationally twists the two gripped housings causing the overall height of the rotational variable height adjustable point specific compression device upper housing to increase in click stops;
and further wherein after an operationally desired height is reached, said rotational variable height adjustable point specific compression device is secured in place and pressure is applied using the belt/strap held in place within the belt/strapguide.

11. The method of making a point specific junctional tourniquet according to claim 10, wherein said upper housing has a plurality of inclination stops located on a spiraling interior surface wall.

12. The method of making a point specific junctional tourniquet according to claim 11, wherein said lower housing further includes a plurality of spiraling mating inclination stops surface capable of mating with said upper housing plurality of inclination stops.

13. The method of making a point specific junctional tourniquet according to claim 12, wherein said lower housing has a center post and is nested into said upper housing having a center post and a spring is placed upon said lower housing and upper housing center post to allow expansion and height adjustment of said rotational variable height adjustable point specific compression device.

14. The method of making a point specific junctional tourniquet according to claim 13, wherein said upper housing center post is inserted into said lower housing center post and said upper and lower housings are secured using a screw and screw access plug.

15. The point specific junctional tourniquet according to claim 10, wherein said upper housing further includes belt/strap engaging spikes located along the bottom of the housing.

16. The method of making a point specific junctional tourniquet according to claim 10, wherein making said rotational variable height adjustable point specific compression device further includes the steps of:
(a) providing inclination stop slots located on said upper housing surface;
(b) providing a set screw and further providing a threaded orifice located in said lower housing to accept a set screw; and;
wherein when assembled the rotational variable height adjustable point specific compression device upper housing is placed over the lower housing and secured using said set screw;
further wherein said set screw is then threaded into said threaded orifice, and when in use, the overall height of said rotational variable height adjustable point specific compression device is adjusted by rotationally running through the inclination stop slots, then securing an optimal height with said set screw, and after the operationally desired height is reached, the rotational variable height adjustable point specific compression device is secured in place and pressure is applied using the belt/strap held in place within the belt/strap guide.

17. The method of making a point specific junctional tourniquet according to claim 16, wherein said upper housing further includes a center post and a spring set on said center post, and.

18. The method of making a point specific junctional tourniquet according to claim 10, further comprising the step of providing a rotational variable height adjustable point specific compression device with a smartphone application.

19. The method of making a point specific junctional tourniquet according to claim 18, wherein said rotational variable height adjustable point specific compression device provided with a smartphone application, further includes a smartphone application having a menu system including:
(a) a dial 9-1-1/find button;
(b) a tourniquet operation instructions button; and
(c) a tourniquet training video button;
wherein when in an emergency situation event a user can push the 9-1-1 button to alert authorities and push the tourniquet operation instructions button to follow a step by step set of instructions and guide to using said rotational variable height adjustable point specific compression device provided.

\* \* \* \* \*